(12) United States Patent
Biber

(10) Patent No.: US 9,610,050 B2
(45) Date of Patent: Apr. 4, 2017

(54) IMAGING DEVICE FOR A JOINT OF A HUMAN

(75) Inventor: Stephan Biber, Erlangen/Frauenaurach (DE)

(73) Assignee: Siemens Aktiengesellschaft, München (DE)

( * ) Notice: Subject to any disclaimer, the term of this patent is extended or adjusted under 35 U.S.C. 154(b) by 453 days.

(21) Appl. No.: 13/441,769

(22) Filed: Apr. 6, 2012

(65) Prior Publication Data

US 2013/0097780 A1    Apr. 25, 2013

(30) Foreign Application Priority Data

Apr. 8, 2011 (DE) .................. 10 2011 007 041

(51) Int. Cl.
*A61B 6/04* (2006.01)
*G01R 33/34* (2006.01)
*A61B 5/055* (2006.01)
*A61B 5/00* (2006.01)

(52) U.S. Cl.
CPC .............. *A61B 6/04* (2013.01); *A61B 5/0555* (2013.01); *A61B 5/4528* (2013.01); *A61B 5/4585* (2013.01); *A61B 6/0421* (2013.01); *G01R 33/34046* (2013.01)

(58) Field of Classification Search
CPC ....... A61B 6/04; A61B 6/0407; A61B 6/0442; A61B 6/0421; A61B 5/6828; A61B 5/6835; A61B 5/70; A61B 5/702; A61B 5/704; A61B 5/4858; A61B 5/4528; A61B 5/0555; A61G 7/0503; A61G 7/065; A61G 7/075; A61G 7/0755; A61G 13/1235; A61G 13/124; A61G 13/1245; A61G 13/125; A61G 13/1295
USPC ...... 5/601, 612, 624, 648; 378/208; 600/415
See application file for complete search history.

(56) References Cited

U.S. PATENT DOCUMENTS

| | | | | | |
|---|---|---|---|---|---|
| 3,957,262 | A | * | 5/1976 | McReynolds | ...................... 5/637 |
| 4,827,496 | A | * | 5/1989 | Cheney | ......................... 378/180 |
| 4,979,949 | A | * | 12/1990 | Matsen, III | ............ A61B 17/15 414/9 |
| 5,063,918 | A | * | 11/1991 | Guhl | .................. A61B 17/6425 602/40 |
| 5,349,956 | A | * | 9/1994 | Bonutti | .......................... 600/425 |
| 6,003,175 | A | * | 12/1999 | Couch | ............................... 5/601 |

(Continued)

OTHER PUBLICATIONS

Merriam-Webster, definition of "fasten", http://www.merriam-webster.com/dictionary/fasten.*

(Continued)

*Primary Examiner* — Nicholas Polito
(74) *Attorney, Agent, or Firm* — Lempia Summerfield Katz LLC

(57) ABSTRACT

An imaging device for a joint of a human is made of an HF transparent material. The imaging device has a base element that may be fastened to a patient bed of a magnetic resonance system. The imaging device includes a bearing element, in which a joint region of an extremity of the human may be supported when the base element is fastened to the patient bed. The bearing element and the base element are connected movably to each other by a guiding structure such that when the base element is fastened to the patient bed, the bearing element may be positioned in a plurality of defined positions relative to the base element.

6 Claims, 3 Drawing Sheets

(56) References Cited

U.S. PATENT DOCUMENTS

| | | | | |
|---|---|---|---|---|
| 6,442,777 | B1 * | 9/2002 | Pauli | 5/601 |
| 6,826,794 | B2 * | 12/2004 | Mahoney | A61G 13/12 |
| | | | | 5/621 |
| 7,947,862 | B2 * | 5/2011 | Livorsi | A61B 17/135 |
| | | | | 128/845 |
| 2011/0030698 | A1 | 2/2011 | Kaufman et al. | |

OTHER PUBLICATIONS

German Office Action dated Oct. 28, 2011 for corresponding German Patent Application No. DE 10 2011 007 041.9 with English translation.

Noras MRI Products GmbH, Webpage, Orthopädische Untersuchungsschienen-Coils, http://www.noras.de/main/index.php?webcode=Othopedic_motion_bar&PHPSESSID, Jul. 2, 2011.

* cited by examiner

IMAGING DEVICE FOR A JOINT OF A HUMAN

This application claims the benefit of DE 10 2011 007 041.9, filed on Apr. 8, 2011.

BACKGROUND

The present embodiment relates to an imaging device for a joint of a human.

An imaging device is known from, for example, the NORAS 8 Ch CPC coil.

In magnetic resonance tomography, images with a high signal-to-noise ratio (SNR) are recorded with local coils. Local coils are antenna systems that are attached in the immediate vicinity on (anterior) or under (posterior) the patient. In case of a magnetic resonance measurement, excited cores in the individual antennas of the local coil induce a voltage that is amplified via a low-noise pre-amplifier (LNA) and forwarded (e.g., by cable) to an evaluation device.

In magnetic resonance tomography, a "coil" may be an antenna system including an antenna element or a plurality of antenna elements. The individual antenna elements may be embodied as loop antennas, butterfly antennas or saddle coils. A coil includes, for example, the antenna elements, the pre-amplifier or pre-amplifiers, further electronics such as, for example, sheath-wave traps, cabling, housing or embedding material and a cable with a plug, using which the coil is connected to the evaluation device.

Special coils may be used for imaging in the region of the extremities (e.g., in the lower extremities (knee, foot) of a human). For example, the requirements of orthopedic imaging make it necessary to arrange the joint in different defined positions (e.g., the knee in different angles and/or the knee or ankle joint slightly twisted or under loading). This "functional imaging" is becoming of increasing importance for orthopedic examinations.

In the prior art, the body coil may be used for reception. A flexible receive coil is used, and the knee is brought into different positions with cushions or in free movement. These approaches are very improvisatorial and due to the poor degree of reproducibility, unsuitable for clinical applications.

The imaging device may be used to bring the knee of a human into defined positions. The defined positioning relates to the joint in question. In addition, with the imaging device, defined positioning with respect to the magnetic resonance tomography system may not automatically be achieved.

SUMMARY AND DESCRIPTION

The present embodiments may obviate one or more of the drawbacks or limitations in the related art. For example, an imaging device for a joint of a human supports functional imaging in a simple and reliable way with respect to the positioning of the joint and the positioning in the magnetic resonance system.

According to the present embodiments, the following features are provided with an imaging device for a joint of a human. In one embodiment, the imaging device is made of an HF transparent material. In another embodiment, the imaging device includes a base element that may be fastened to a patient bed of a magnetic resonance system. In one embodiment, the imaging device includes a bearing element, in which a joint region of an extremity of the human may be supported when the base element is fastened to the patient bed. In another embodiment, the bearing element and the base element are movably connected to each other by a guiding structure such that when the base element is fastened to the patient bed, the bearing element may be positioned in a plurality of defined positions relative to the base element.

The bearing element may be adjustable relative to the base element in several degrees of freedom independently of each other. For example, a translational degree of freedom in combination with at least one rotational degree of freedom may be provided. Alternatively, the guiding structure may be embodied as a guiding structure restricting five degrees of freedom so that one single degree of freedom remains for a movement of the bearing element relative to the base element.

The wording "as a guiding structure restricting five degrees of freedom" does not provide that the bearing element may only be positioned in a single translational direction or only about one single axis of rotation relative to the base element. This wording may provide that movements are coupled with each other such that positioning in one of the three possible translational degrees of freedom establishes the positioning in the two other translational degrees of freedom and in the three rotational degrees of freedom.

If the guiding structure is embodied as a guiding structure restricting five degrees of freedom, the imaging device may include a drive, by which the bearing element is adjustable relative to the base element when the base element is fastened to the patient bed. Alternatively, when the base element is fastened to the patient bed, the bearing element may be loaded to a neutral position relative to the base element, and when the base element is fastened to the patient bed, the bearing element may be moved from the neutral position into a loaded position by the muscle strength of the extremity of the human with the joint supported in the bearing element.

Regardless of whether the guiding structure is embodied as a guiding structure restricting five degrees of freedom or not, when the base element is fastened to the patient bed, the bearing element may be manually adjustable relative to the base element. The defined positions may be discrete positions, and the bearing element may be lockable or latchable in the defined positions relative to the base element. Alternatively, the defined positions may form a continuum, and the bearing element may be fixed in the defined positions relative to the base element by bracing.

In one embodiment, the transfer of the bearing element from one of the defined positions into another of the defined positions involves a translational movement. The translational movement may take place exclusively vertically.

The bearing element may alternatively be embodied as a bearing element for a knee, an ankle joint, an elbow joint or a wrist joint of the human. If the bearing element is embodied as a bearing element for a knee of a human, a foot support and/or a trunk support may be arranged at the base element. The foot support and/or the trunk support, on a vertical translational movement of the bearing element, are moved horizontally relative to the base element.

In one embodiment, the bearing element encloses the joint of the human in a ring-like manner. The bearing element may, for example, be embodied as a bearing element that may be opened.

In individual cases, the imaging device may be embodied as a purely mechanical device (e.g., without coil elements for the imaging). However, a local coil for magnetic resonance applications is arranged in the bearing element. If present, the local coil may alternatively be embodied as a pure transmit coil, as a pure receive coil, or as a combined transmit and receive coil.

DETAILED DESCRIPTION OF THE DRAWINGS

Figure 1:
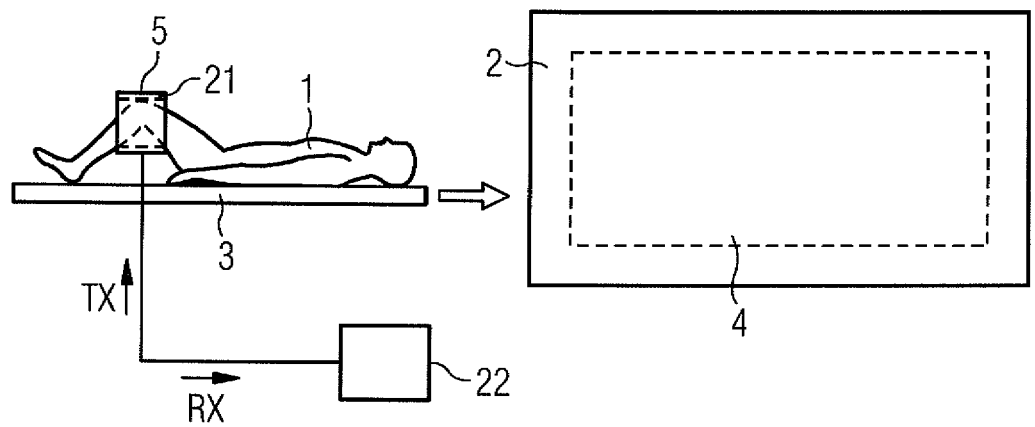
FIG. 1 shows a magnetic resonance system.
Figure 2:
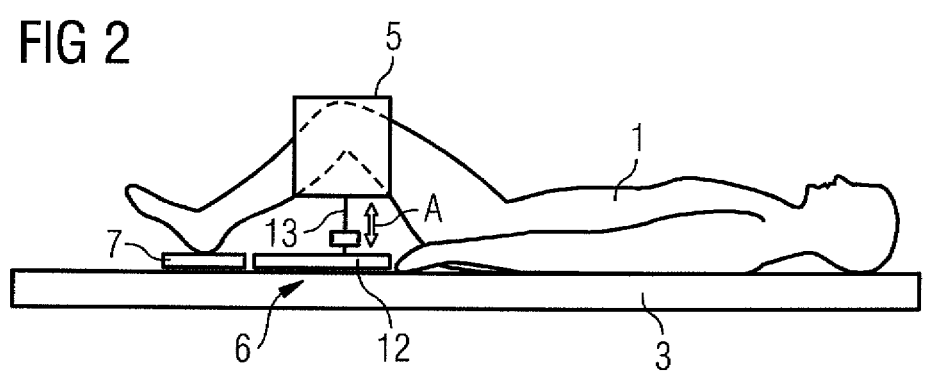
FIG. 2 shows a patient bed with an imaging device.

According to FIGS. 1 and 2, a human 1 is to be examined in a magnetic resonance system 2. The human 1 is arranged on a patient bed 3. The patient bed 3, including the human 1 arranged thereupon, is transported into a region under examination 4 of the magnetic resonance system 2.

Magnetic resonance examinations are performed for an extremely wide variety of purposes. In the present case, a joint of an extremity of the human 1 is to be examined for the purposes of a functional orthopedic examination. The joint of the human 1 is arranged in a bearing element 5 of an imaging device 6.

The joint of the human 1 to be examined may be, for example, a knee joint. Reference is subsequently made to a foot support 7 and/or a trunk support 7' of the imaging device 6, but the joint of the human 1 may be any other joint. If the foot support 7 and the trunk support 7' are not involved, alternatively to the knee joint, the joint of the human 1 could be an ankle joint, an elbow joint or a wrist joint.

The imaging device 6 includes the bearing element 5. The joint of the human 1 may be supported in the bearing element 5. The bearing element 5 may enclose the joint of the human 1 in a ring-like manner as shown in the representation in FIG. 2. Alternatively, the bearing element 5 may, for example, be embodied in a trough shape.

Figure 3:
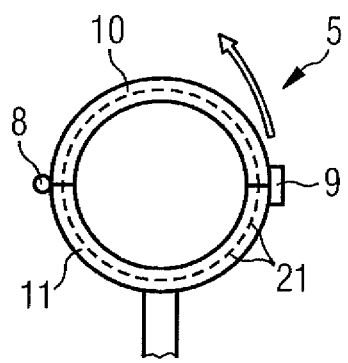
FIGS. 3 and 4 show embodiments of a bearing element.
Figure 4:
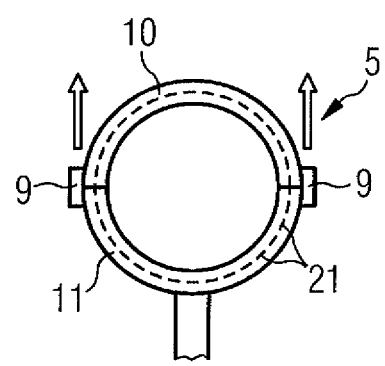

In the case of a ring-like embodiment, the bearing element may be opened. For example, as shown in the representation in FIG. 3, the bearing element 5 may have a hinge 8 on one side and a plug 9 on the other side so that an upper part 10 of the bearing element 5 may be folded upward away from the lower part 11 of the bearing element 5 using the hinge 8 like the lid of a storage chest. Alternatively, as shown in FIG. 4, the bearing element 5 may have a plug 9 on both sides so that the upper part 10 may be completely removed from the lower part 11.

The imaging device 6 also includes a base element 12. The base element 12 may be fastened to the patient bed 3 (e.g., latched or plugged thereto). The base element 12 is connected to the bearing element 5 by a guiding structure 13. The joint of the human 1 may be supported in the bearing element 5 of the imaging device 6. The supporting function (e.g., the introduction of the joint into the bearing element 5) and also the later removal of the joint from the bearing element 5 may be effected while the base element 12 is fastened to the patient bed 3.

The bearing element 5 is connected movably to the base element 12 by the guiding structure 13. The movable connection is such that the bearing element 5 may be positioned in a plurality of defined positions relative to the base element 12, and more specifically, while the base element 12 is fastened to the patient bed 3. Therefore, the base element 12 may be fastened to the patient bed 3, and the desired defined position of the bearing element 5 may be set relative to the base element 12. The adjustability of the bearing element 5 relative to the base element 12 is indicated in FIG. 2 by a corresponding double arrow A.

The base element 12, the guiding structure 13, the bearing element 5, and, if present, further elements of the imaging device 6 (e.g., the foot support 7 and the trunk support 7') are made of an HF transparent material (e.g., a plastic). As a result, therefore, the entire imaging device 6 is made of an HF transparent material so the imaging device 6 does not exert a negative influence on the magnetic resonance data acquisition.

Figure 5:
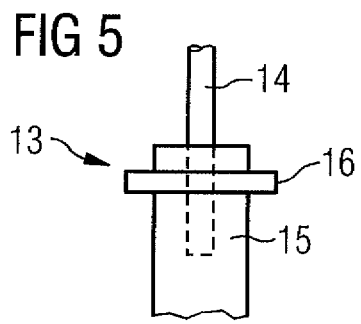
FIGS. 5 to 7 show embodiments of manually adjustable imaging devices.

The bearing element 5 may be manually adjustable relative to the base element 12 and more specifically, when the base element 12 is fastened to the patient bed 3. The defined positions may, for example, form a continuum, and the bearing element 5 may be fixed in the defined positions relative to the base element 12 by bracing. For example, the bearing element 5 may be connected to the base element 12, as shown in FIG. 5, by a rod 14 that is mounted displaceably in a guide 15. The rod 14 may, for example, be fixed by a bracing element 16. The bracing element 16 may be configured as a bracing element 16 that may be actuated without tools (e.g., as an eccentrically mounted clamping lever). In the embodiment shown in FIG. 5, the rod 14 and the guide 15 are parts of the guiding structure 13.

Figure 6:
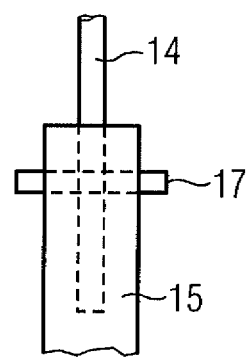
Figure 7:
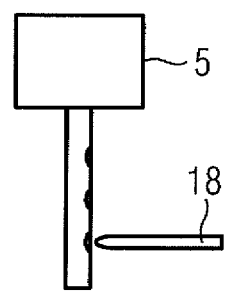

Alternatively, in the case of manual adjustability, the defined positions may be discrete positions. The bearing element 5 may, for example, be lockable in the defined positions relative to the base element 12, as shown in FIG. 6 (e.g., using a holding pin 17 that is to be removed to be able to move the bearing element 5 relative to the base element 12). As an alternative to locking, the bearing element 5 may, for example, be latched relative to the base element 12, as shown in FIG. 7, when the bearing element 5 reaches one of the defined positions. The difference from locking as shown in FIG. 6 includes that the bearing element 5 may be moved out of the respective defined position by exerting a sufficiently high force without previously having manually to loosen a latching element 18 implementing the latching. In the case of FIGS. 6 and 7, the bearing element 5 may be moved relative to the base element 12 while the base element 12 is fastened to the patient bed 3.

Mixed forms are also provided. For example, the bearing element 5 may be moved upward (e.g., against the weight force) without previously loosening a latching mechanism, while the insertion of the bearing element 5 is only possible if a latching mechanism is loosened.

The transfer of the bearing element 5 relative to the base element 12 from one of the defined positions into another of the defined positions encompasses a translational movement, as shown in FIG. 2. Where this relates to the translational movement of the bearing element 5 relative to the base element 12, the translational movement of the bearing element 5 relative to the base element 12 may only have one single degree of freedom. As shown in FIG. 2, the corresponding degree of freedom may, for example, be exclusively vertically directed and so the corresponding movement may take place exclusively vertically.

In the case of manual adjustability, in addition to a translational degree of freedom (whether this is exclusively vertically directed or not), up to three further rotational degrees of freedom (e.g., a twisting of the bearing element 5 relative to the base element 12) are possible. Alternatively, the guiding structure 13 may be embodied as a guiding structure restricting five degrees of freedom 13 so that only one single degree of freedom remains for the movement of the bearing element 5 relative to the base element 12 (e.g., the exclusively vertical translational movement).

Figure 8:
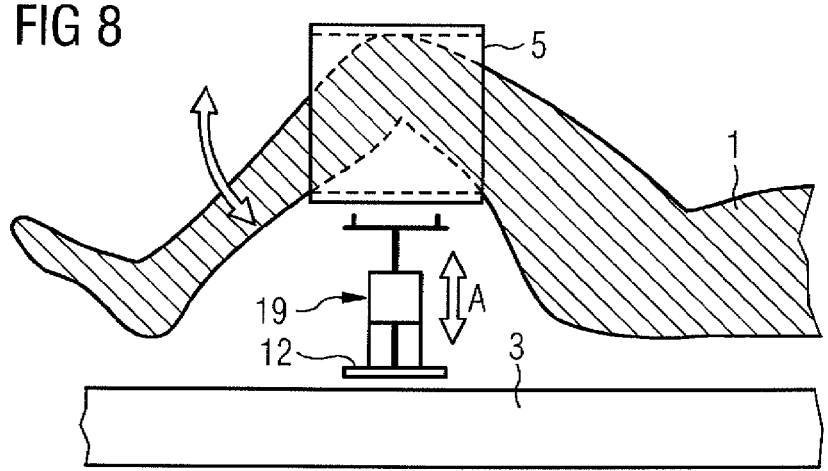
FIG. 8 shows one embodiment of a patient bed with an imaging device adjustable by a drive.

Alternatively to manual adjustability, the imaging device 6 may include, as shown in FIG. 8, a drive 19, using which the bearing element 5 may be adjusted relative to the base element 12. In connection with the adjustability by the drive 19, the guiding structure 13 is embodied such that the guiding structure 13 only permits one single degree of freedom (e.g., the exclusively vertical translational adjustment of the bearing element 5 relative to the base element 12). In connection with FIG. 8, adjustability is also possible while the base element 12 is fastened to the patient bed 3. The drive 19 may be embodied as required. For example, the drive 19 may be embodied as a pneumatic drive or as an inflatable cushion.

Figure 9:
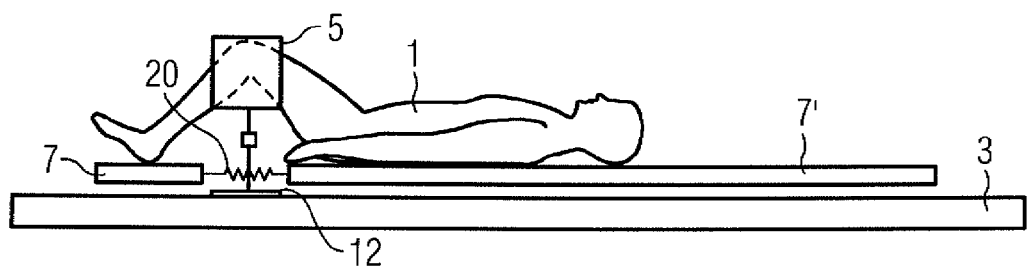
FIGS. 9 and 10 show one embodiment of a patient bed with a spring-loaded imaging device.

As shown in FIG. 9, one alternative to adjustability of the bearing element 5 relative to the base element 12 using a drive 19 includes that the bearing element 5 is loaded to a neutral position relative to the base element 12 when the base element 12 is fastened to the patient bed 3. For example, as shown in FIG. 9, a spring device 20 may be provided. Alternatively, for example, a loading weight may exert the corresponding loading to the neutral position via a cable pull.

Figure 10:
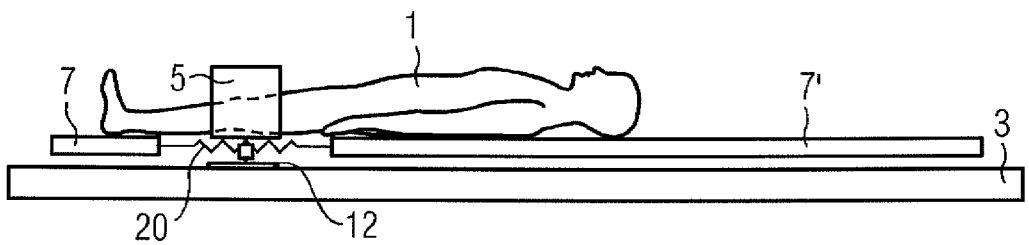

In the case where the bearing element 5 is loaded to a neutral position relative to the base element 12, as shown in FIG. 10, the bearing element 5 may be moved out of the neutral position relative to the base element 12 by the muscle strength of the corresponding extremity of the human 1 with the joint supported in the imaging device 6 (e.g., the bearing element 5) into a loaded position.

Also in connection with the embodiment in FIGS. 9 and 10, the bearing element 5 is adjustable relative to the base element 12 while the base element 12 is fastened to the patient bed 3. The guiding structure 13 may restrict five degrees of freedom so that only one single degree of freedom (e.g., the exclusively vertical translational mobility) remains for the adjustability.

The bearing element 5 may be moved exclusively vertically relative to the base element 12. In cases when the imaging device 6 is intended to support a knee joint, additionally the foot support 7, and alternatively or additionally the trunk support 7', is provided. According to FIGS. 2, 9 and 10, the foot support 7 and/or the trunk support 7' are arranged such that, on a vertical movement of the bearing element 5 relative to the base element 12, the foot support 7 and/or the trunk support 7' are moved horizontally relative to the base element 12. For example, a downward movement of the bearing element 5 (e.g., onto the base element 12) is coupled with a movement of the foot support 7 and/or the trunk support 7' away from the base element 12.

The bearing element 5 has other functions in addition to supporting the joint of the human 1. For example, as shown in FIGS. 3 and 4, a local coil 21 is arranged in the bearing element 5 for magnetic resonance applications. The local coil 21 may be embodied as a pure transmit coil. In this case, although excitation signals TX are transmitted to the local coil 21 by a control and evaluation device 22 of the magnetic resonance system 2, the reverse (e.g., the transmission of magnetic resonance signals RX received by the local coil 21 to the control and evaluation device 22) does not take place. Alternatively, the local coil 21 may be embodied vice versa as a pure receive coil. In this case, although magnetic resonance signals RX received by the local coil 21 are transmitted to the control and evaluation device 22, the reverse (e.g., the transmission of excitation signals TX by the control and evaluation device 22 to the local coil 21) does not take place. Alternatively, the local coil 21 may be embodied as both a transmit coil and a receive coil. Therefore, both excitation signals TX to be transmitted to the local coil 21 and magnetic resonance signals RX received by the local coil 21 may be transmitted.

The imaging device 6 according to the present embodiments permits efficient functional orthopedic imaging in magnetic resonance systems.

The above description is exclusively for purposes of explaining the present embodiments. The scope of protection of the present invention is exclusively determined by the attached claims.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An imaging device for a joint of a human, the imaging device comprising:
   a base element that is fastenable to a patient bed of a magnetic resonance system; and
   a bearing element, in which a joint region of an extremity of the human is supportable when the base element is fastened to the patient bed, the patient bed including a patient bearing surface on which the human is positionable; and
   a foot support, a trunk support, or a combination thereof arranged on the base element, the foot support, the trunk support, or the combination thereof being moved in a first direction relative to the base element when the bearing element moves in a second direction relative to the base element, the second direction being different than the first direction,
   wherein the bearing element and the base element are connected movably to each other by a guiding structure such that when the base element is fastened to the patient bed, the bearing element is positionable in a plurality of defined positions relative to the base element,
   wherein the guiding structure is configured as a guiding structure restricting five degrees of freedom so that a single degree of freedom remains for a movement of the bearing element relative to the base element,
   wherein when the base element is fastened to the patient bed, the bearing element is loaded to a neutral position relative to the base element, and
   wherein when the base element is fastened to the patient bed, the bearing element is transferable from the neutral position into a loaded position by a force, and transferable from the loaded position into the neutral position in response to the force being removed.

2. The imaging device as claimed in claim 1, wherein the bearing element encloses the joint of the human in a ring-like manner.

3. The imaging device as claimed in claim 2, wherein the bearing element is openable.

4. The imaging device as claimed in claim 3, wherein a local coil for magnetic resonance applications is arranged in the bearing element.

5. The imaging device as claimed in claim 1, wherein a local coil for magnetic resonance applications is arranged in the bearing element.

6. The imaging device as claimed in 5, wherein the local coil comprises a pure transmit coil, a pure receive coil, or a combined transmit and receive coil.

* * * * *

UNITED STATES PATENT AND TRADEMARK OFFICE
CERTIFICATE OF CORRECTION

PATENT NO. : 9,610,050 B2
APPLICATION NO. : 13/441769
DATED : April 4, 2017
INVENTOR(S) : Stephan Biber Page 1 of 2

It is certified that error appears in the above-identified patent and that said Letters Patent is hereby corrected as shown below:

On the Title Page

Under abstract "6 Claims, 3 Drawing Sheets" should read --11 Claims, 3 Drawing Sheets--.

In the Claims

Column 6, Line 26-Column 7, Line 6, (approx.), should read:

--1. An imaging device for a joint of a human, the imaging device comprising:
a base element that is fastenable to a patient bed of a magnetic resonance system; and
a bearing element, in which a joint region of an extremity of the human is supportable when the base element is fastened to the patient bed, the patient bed including a patient bearing surface on which the human is positionable; and
a foot support, a trunk support, or a combination thereof arranged on the base element, the foot support, the trunk support, or the combination thereof being moved in a first direction relative to the base element when the bearing element moves in a second direction relative to the base element, the second direction being different than the first direction,
wherein the bearing element and the base element are connected movably to each other by a guiding structure such that when the base element is fastened to the patient bed, the bearing element is positionable in a plurality of defined positions relative to the base element,
wherein the guiding structure is configured as a guiding structure restricting five degrees of freedom so that a single degree of freedom remains for a movement of the bearing element relative to the base element,
wherein when the base element is fastened to the patient bed, the bearing element is loaded to a neutral position relative to the base element, and
wherein when the base element is fastened to the patient bed, the bearing element is transferable from the neutral position into a loaded position by a force, and transferable from the loaded position into the neutral position in response to the force being removed.

Signed and Sealed this
Thirty-first Day of March, 2020

Andrei Iancu
*Director of the United States Patent and Trademark Office*

2. The imaging device as claimed in claim 1, wherein the transfer of the bearing element from one defined position of the plurality of defined positions into another defined position of the plurality of defined positions involves a translational movement, and
wherein the translational movement takes place exclusively vertically.

3. The imaging device as claimed in claim 2, wherein the bearing element is configured as a bearing element for a knee of the human, and
wherein a foot support, a trunk support, or a combination thereof are arranged on the base element, the foot support, the trunk support, or the combination thereof being moved horizontally relative to the base element on a vertical translational movement of the bearing element.

4. The imaging device as claimed in claim 3, wherein the bearing element encloses the joint of the human in a ring-like manner.

5. The imaging device as claimed in claim 2, wherein the bearing element encloses the joint of the human in a ring-like manner.

6. The imaging device as claimed in claim 2, wherein a local coil for magnetic resonance applications is arranged in the bearing element.

7. The imaging device as claimed in claim 1, wherein the bearing element encloses the joint of the human in a ring-like manner.

8. The imaging device as claimed in claim 7, wherein the bearing element is openable.

9. The imaging device as claimed in claim 8, wherein a local coil for magnetic resonance applications is arranged in the bearing element.

10. The imaging device as claimed in claim 1, wherein a local coil for magnetic resonance applications is arranged in the bearing element.

11. The imaging device as claimed in 10, wherein the local coil comprises a pure transmit coil, a pure receive coil, or a combined transmit and receive coil.--.